(12) United States Patent
Roux et al.

(10) Patent No.: US 8,062,859 B2
(45) Date of Patent: Nov. 22, 2011

(54) METHOD FOR SCREENING ANTICANCER SUBSTANCES, SET OR KIT FOR IMPLEMENTING SAID METHOD

(75) Inventors: Pierre Roux, Saint-Gely-du Fesc (FR); Marion De Toledo, Montpellier (FR)

(73) Assignee: Centre National de la Recherche Scientifique (CNRS), Paris (FR)

( * ) Notice: Subject to any disclaimer, the term of this patent is extended or adjusted under 35 U.S.C. 154(b) by 320 days.

(21) Appl. No.: 11/917,522

(22) PCT Filed: Jun. 14, 2006

(86) PCT No.: PCT/FR2006/050561
§ 371 (c)(1),
(2), (4) Date: Jul. 18, 2008

(87) PCT Pub. No.: WO2006/134305
PCT Pub. Date: Dec. 21, 2006

(65) Prior Publication Data
US 2009/0162874 A1    Jun. 25, 2009

(30) Foreign Application Priority Data
Jun. 14, 2005  (FR) ...................... 05 51616

(51) Int. Cl.
*G01N 33/574* (2006.01)
*G01N 33/566* (2006.01)

(52) U.S. Cl. ........................ 435/7.23; 436/501

(58) Field of Classification Search ................ None
See application file for complete search history.

(56) References Cited

FOREIGN PATENT DOCUMENTS
WO    WO2006/078717    *    7/2006

OTHER PUBLICATIONS

Nam et al (Clinical and Experimental Metastasis, 2004, vol. 21, pp. 49-56).*
Shimoyama et al (Cancer Research, 1989, vol. 49, pp. 2128-2133).*
Guan et al (Cancer Research, 2000, vol. 60, pp. 749-755).*
Kerr and Thorpe (Immunochemistry LabFax, 1994, p. 171).*
Sternberger et al, The Journal of Histochemistry and Cytochemistry, 1970, vol. 18, pp. 315-333.*
Mueller et al, Cancer Research, 2000, vol. 60, pp. 156-163.*
de Vries et al, British Journal of Cancer, 1995, vol. 71, pp. 271-277.*
Kinsella et al (Clinical and Experimental Metastasis, 1994, vol. 12, pp. 335-342).*
Frixen et al (The Journal of Cell biology, 1991, vol. 113, pp. 173-185).*
Kerr and Thorpe (Immunochemistry LabFax, 1994, p. 194.*
Carter et al.; 2004 American Society for Nutritional Sciences.
Muller et al.; Oncogene (2002) 21,pp. 6049-6058.
The Journal of Cell Biology vol. 154, No. 2, Jul. 23, 2001, pp. 369-387.

* cited by examiner

*Primary Examiner* — Karen Canella
(74) *Attorney, Agent, or Firm* — Young & Thompson

(57) ABSTRACT

A method for screening anticancer substances comprising the following steps:
a) obtaining a culture of tumour cells which do not express E-cadherin on their cell membrane;
b) bringing the cells obtained at step a) into contact with a candidate substance or a combination of candidate substances;
c) detecting, in the culture of cells obtained at the end of step b), the presence of E-cadherin at the cell surface;
d) positively selecting the candidate substance or combination of candidate substances when the E-cadherin has been detected at step c).

9 Claims, 2 Drawing Sheets

Figure 1:
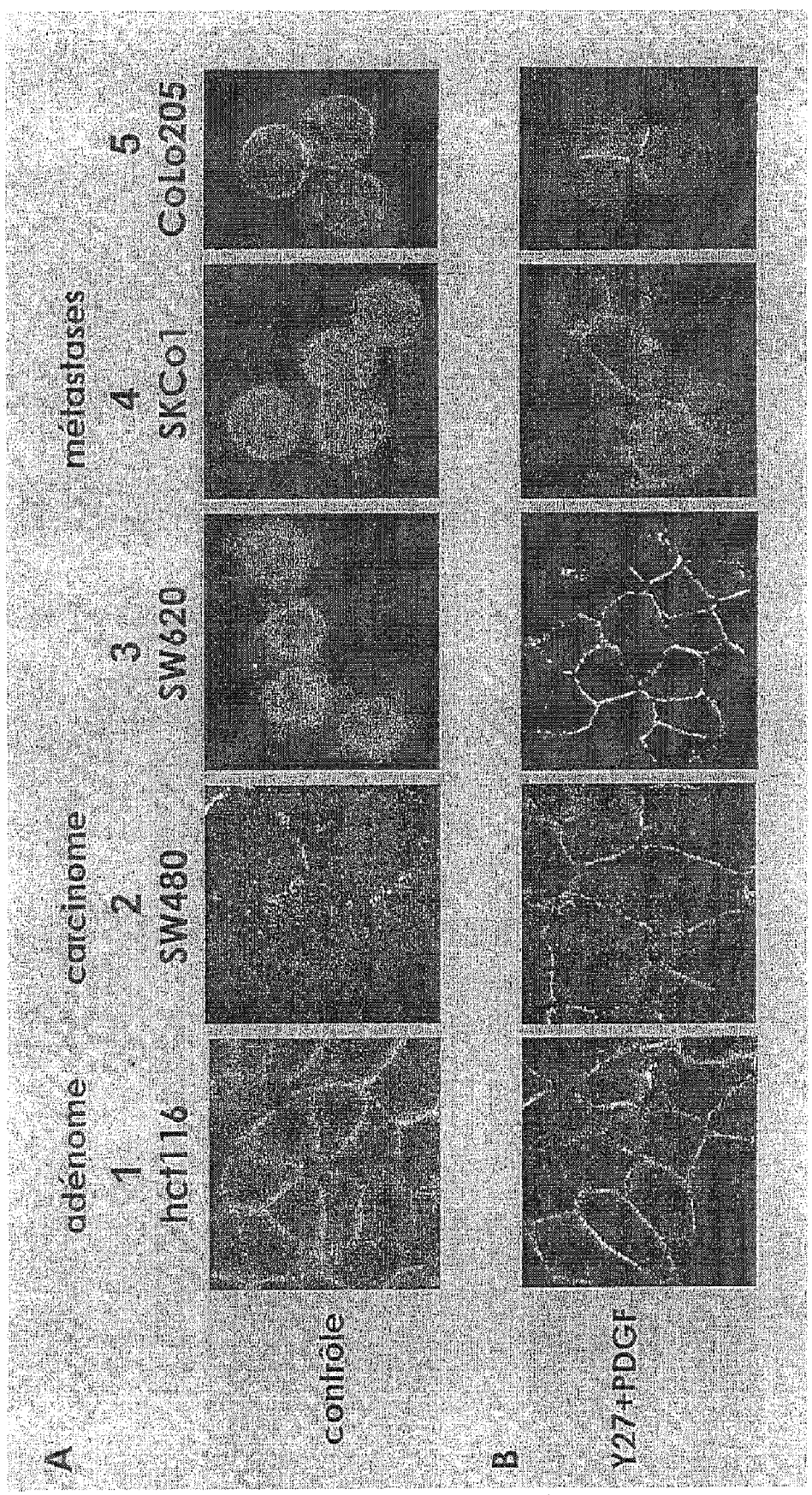

METHOD FOR SCREENING ANTICANCER SUBSTANCES, SET OR KIT FOR IMPLEMENTING SAID METHOD

SUMMARY OF THE INVENTION

This invention pertains to the field of the identification of molecules of therapeutic interest for cancer treatment.

The object of this invention is a method for screening anticancer substances comprising the following steps:
a) obtaining a culture of tumour cells which do not express E-cadherin on their cell membrane;
b) bringing the cells obtained at step a) into contact with a candidate substance or a combination of candidate substances;
c) detecting, in the cell culture obtained at the end of step b), the presence of E-cadherin at the cell surface;
d) positively selecting the candidate substance or the combination of candidate substances when E-cadherin has been detected at step c).

The object of this invention is also a set or kit for screening anticancer substances comprising:
a) tumour cells which do not express E-cadherin on their cell membrane;
b) a ligand compound of E-cadherin.

The invention also relates to the use of a ligand compound of the extracellular portion of E-cadherin for the in vitro screening of cancerous substances.

PRIOR ART

It is known that, in certain cancers, tumour cells have not only a great ability to proliferate, but also a great capacity for destroying tissue and invading neighbouring tissue, including blood vessels and lymph vessels, then migrating in the circulatory system to tissues in parts of the body far away from the primary tumour. Thus, in certain cancers, tumour cells have the capacity to circulate and form secondary tumours, also called metastases, in tissues distant from the primary tumour.

As stated above, the formation of metastases is a physiological phenomenon involving multiple steps, during which tumour cells leave the primary tumour, invade the cell matrix, penetrate the blood vessels, enter the vascular system by intravasation, then stop their migration in the blood or lymph circulation at a distant site, leave the circulation by extravasation, bind to distant tissue and proliferate to form a secondary tumour.

Different molecules are likely to play a role in the formation of metastases, including certain chemokine receptors and integrin receptors.

Notably, it has been shown in the art that certain proteins belonging to the cadherin family are likely to be involved in the physiological mechanisms leading to the formation of metastases.

The cadherin family is a family of proteins that regulate the adhesion of epithelial, endothelial, neural or cancer cells. Different types of cadherins are expressed depending on the tissue, such as (i) N-cadherin, which is mainly expressed by neural cells, endothelial cells and different types of cancer cells; (ii) E-cadherin, which is expressed exclusively by epithelial cells; (iii) P-cadherin, which is found in the skin, in humans; (iv) R-cadherin, which is expressed in the retina.

Due to the involvement of cadherins in cell adhesion, various methods and products have been proposed in the prior art, that are able to modulate the regulation of the cell adhesion of these proteins. Thus, in the American patent application no US 2003/0109454, the applicants suggested to modify the functions of the cadherins using protein modulating agents comprising at least one "HAV" motif, which motif is essential for the interaction between two cadherin molecules, also called homotypic interaction. According to this American patent application, such modulating agents are able to act on cell adhesion and thus facilitate the diffusion of drugs through the tissues. The American patent application no US 2003/109454 also describes a method that makes it possible to select agents modulating cell adhesion, by positively selecting candidate compounds binding to antibodies directed against a sequence containing an HAV adhesion motif. Also, the American patent application no US 2002/0192724 describes the use of proteins, particularly antibodies, which bind to certain extracellular regions of the cadherins, in order to modulate the adhesion of T lymphocytes to cells expressing cadherins.

Mention can also be made of the American U.S. Pat. No. 6,468,790 which describes the protein sequences that constitute metastatic markers for breast and colon cancers. Among the many markers described, E-cadherin is mentioned, due to the fact that (i) messenger RNA encoding E-cadherin is found in the cell extracts of a non-metastatic breast cancer cell line (MCF7), but (ii) messenger RNA encoding E-cadherin is not found in the cell extracts of two non-metastatic breast cancer cell lines (MDA-MB-231 and MDA-MB-435). In the American U.S. Pat. No. 6,468,790, the applicants propose detecting the level of expression of these protein markers, or the expression level of their corresponding genes or messenger RNAs, in order to determine the cancers that are liable to spread by forming metastases. American U.S. Pat. No. 6,468,790 also proposes screening methods for agents likely to have an antimetastatic effect. According to these screening methods, the candidate compound to be tested is incubated with cancerous cells and the expression level of the protein marker, or of the corresponding gene or messenger RNA, is determined. The level of expression of the marker protein is determined either (i) by incorporating labelled amino acids into the cells, then detecting the labelled marker proteins on a polyacrylamide gel, or (ii) by detecting the marker proteins with specific antibodies, by immunoblotting (also called Western blot tests). The expression level of the gene encoding the marker protein of interest is determined by analysing the messenger RNAs, using the well known Northern blot technique.

However, the mechanisms of the initiation and development of cancerous metastases cannot be explained by the involvement of E-cadherin alone, and many other factors are known to be involved in these mechanisms. Thus, in the American U.S. Pat. No. 6,468,790, although an inactivation of expression of proteins such as E-cadherin by metastatic breast cancer cells is shown, no result is presented to show (i) that inactivation of E-cadherin expression is likely to transform a cancer cell into a metastatic cancer cell, or on the contrary (ii) that an activation of E-cadherin expression is likely to transform a metastatic cancer cell into a non-metastatic cancer cell.

Thus, to the knowledge of the applicant, to date no technical means exists that would make it possible to determine the potentially metastatic nature of a cancer cell.

Moreover, to the knowledge of the applicant, no method exists that makes it possible to screen antimetastatic compounds under conditions close to those of cell physiology.

However, the formation of metastases of cancerous cells is a bad prognosis for the patient, because this situation necessitates, due to the geographical dispersion of the metastases, the use of systemic antimetastatic treatments, exclusively.

There is thus a need in the art for identifying new compounds able to inhibit the migration of tumour cells and thus to prevent the formation of metastases, and consequently, to identify reliable screening methods that make it possible to select these new antimetastatic compounds.

DESCRIPTION OF THE INVENTION

This invention provides a method for screening anticancer substances, and more specifically for screening antimetastatic substances.

Surprisingly, the applicant has shown that a strict correlation exists between the induction of the loss of migratory capacity and invasive capacity of initially metastatic cells, and the induction of the formation of intercellular junctions involving the presence of E-cadherin. The applicant's demonstration of this surprising correlation allowed him to design and develop a method for screening antimetastatic substances which makes use of initially metastatic cancer cells, and which comprises a step during which the presence of E-cadherin exposed at the cell surface of cells previously treated with a candidate substance, or with a combination of candidate substances, is detected.

The object of this invention is a method for screening anticancer substances comprising the following steps:
a) obtaining a culture of tumour cells which do not express E-cadherin on their cell membrane;
b) bringing the cells obtained at step a) into contact with a candidate substance or a combination of candidate substances;
c) detecting, in the cell culture obtained at the end of step b), the presence of E-cadherin at the cell surface;
d) positively selecting the candidate substance or combination of candidate substances when E-cadherin has been detected at step c).

The term "anticancer substances" as used according to the present invention is understood to mean substances able to make cancerous cells with a metastatic cell phenotype revert to a non-metastatic phenotype. Among the anticancer substances likely to be positively selected by the method of the invention, some of them will not modify the proliferation capacity of initially metastatic cancer cells. But other anticancer substances likely to be positively selected by the method of the invention will be able both to induce a reversion of the metastatic phenotype to a non-metastatic phenotype and to inhibit or block the proliferation capacity of initially cancerous and metastatic cells.

Due to the strict correlation which has been shown according to the invention between the inhibition of the invasive power of the cancerous cells and the presence of exposed E-cadherin on the surface of the cell membranes, the aforementioned method enables screening of anticancer candidate substances, and in all instances antimetastatic candidate substances, under conditions in which the cells tested are in a situation close to their in vivo physiological situation.

In particular, the method of the invention makes it possible to screen anticancer substances, especially antimetastatic substances, which do not act directly on the expression of E-cadherin. Notably, the screening method according to the invention allows positive selection of anticancer substances, especially antimetastatic substances, which are active on various targets in the cell, as long as their antimetastatic capacity is in all instances verified by their capacity to make the phenotype of treated cells revert to a non-metastatic cell phenotype, by forming intercellular junctions, which is determined by detecting the presence of E-cadherin at the surface of the cell membranes.

The aforementioned method makes it possible to screen the candidate substances directly on living cells, and thus allows positive selection of substances having the physiological effect of inhibiting or blocking the capacity of the cell to form metastases.

As is shown in the examples, the method of the invention is particularly suitable for the screening of anticancer substances, especially antimetastatic substances that are active on the metastatic cancer cells derived from epithelial cells. It has thus been shown that the method of the invention enables successful selection of substances that make mesenchymal cancer cells revert to a phenotype of epithelial cells that are again able to form intercellular junctions.

Another advantage of the method according to the invention is that this method enables positive selection, exclusively of anticancer substances, especially antimetastatic substances, which are not cytotoxic. This is because all the candidate substances that are toxic to cells, since they kill the cells, are not able to induce any physiological change in the cells, and particularly are not able to cause them to revert to the non-metastatic phenotype, with re-formation of intercellular junctions in the presence of E-cadherin. Thus cytotoxic candidate substances will never be positively selected using the method of the invention.

At step a) of the method, it is advantageous to use metastatic tumour cells which do not express E-cadherin, which are derived from epithelial cells. In general, these metastatic cells consist of cells of epithelial origin that have lost their epithelial cell phenotype, and that have acquired cell motility properties due to reorganisation of the cytoskeleton and also due to the formation of new types of contact with the extracellular matrix. All of these phenotype transformations of the initial epithelial cell constitute epithelial-mesenchymal transitions (EMT).

Thus, at step a) of the method, it is advantageous to use metastatic cancer cells, preferably of epithelial origin, which can be selected from established cell lines, or which can be selected from primary culture of metastatic cancer cells, originating from a cell sample or a tissue biopsy taken from a cancer patient.

Among metastatic cancer cell lines, it may be used tumour cells having the capacity to form metastases and that are selected from among the following cell lines: SW620 (ATCC no CCL-227), SKCo-1 (ATCC no HTB-39), CoLo205 (ATCCno CCL-222), and HCT116 (ATCC no CCL-247) rendered p21-deficient.

At step a) of the method, the number of cells plated per culture dish varies depending on the dish used and, where appropriate, the type of cells used, in particular according to the proliferation capacity of the cancer cells used. As an indication, when the cancer cells are plated on conventional 96-well culture plates, 2000 to 30 000 cells can be plated per culture well, preferably 5000 to 20 000 cells per culture well. Those skilled in the art will use their general knowledge to adapt the number of cells, depending on the type of culture container and the type of cancerous cells used.

Thus, the invention method is particularly suitable for screening candidate substances having the ability to block the metastatic capacity of cancerous cells derived from epithelial cells. Thanks to the method of the invention, it is possible to screen physiologically active antimetastatic substances likely to be used in the production of drugs useful in the prevention or treatment of cancers known to disseminate in the form of metastases, especially cancers of epithelial cells such as breast cancers, colorectal cancers, ovarian cancers, bladder cancers, cancers of the neck of the womb, skin cancers including basocellular carcinomas, stomach cancers, epithelial tumours of the thymus, prostate cancers, testicles cancers, lungs cancers, throat cancers, pancreas cancers, liver cancers, bile duct cancers, and bladder cancers.

At step b) of the method, the cells are incubated with a candidate substance or a combination of candidate substances to be tested. In a combination of candidate substances to be tested, one or more of these substances may already be known for their antimetastatic potency. For example, it is possible to use, in a combination of candidate substances to be tested, at least one substance with a known antimetastatic potency, in order to determine the existence of any possible synergy of action between the substance with known activity and the other substance or substances of the said combination of substances.

At step b), the cell culture is brought into contact with the substance or substances to be tested for a variable time period, which, by way of illustration, can vary from 30 minutes to 72 hours.

In general, step b) is carried out by using a series of cell cultures, for example in microplate wells of a known type of cell culture, and incubating each well or each subset of wells with variable concentrations of the substance(s) to be tested. Advantageously, one well or subset of wells is incubated with the culture medium only and serves as a negative control. Advantageously, one well or subset of wells is incubated with a known concentration or series of concentrations of a substance known for its antimetastatic potency and serves as a positive control.

At step c) of the method, the detection of the presence of E-cadherin at the cell membrane surface of the cells in culture can be carried out by those skilled in the art using any known detection technique.

According to a certain embodiment, step c) of detection is carried out on the cells in culture, without prior treatment of the cell cultures.

According to another embodiment, the detection step c) is carried out after prior treatment of the cells in culture, preferably a fixation treatment of the cells in culture, using any cell fixing agent or any combination of cell fixing agents known to those skilled in the art. By way of illustration, at the beginning of step c) of the method, the cells in culture are fixed with formalin, prior to the actual step of E-cadherin detection. The cells are advantageously incubated with the fixing agent for an appropriate period of time, depending on the agent used, for example for a time varying from 1 minute to 1 hour. For formalin, an incubation time period with the fixing agent varying from 5 minutes to 30 minutes, preferably from 5 minutes to 15 minutes, is suitable.

Advantageously, the detection of the presence of extramembranous E-cadherin is carried out, at step c) of the method, by bringing the cells obtained at the end of step b) into contact with a ligand compound of E-cadherin.

When a cell fixing agent is used, it is possible, in a particular embodiment, to treat the fixed cells with saturation proteins in suspension in a buffer, such as serum albumin, including bovine serum albumin (BSA), for a duration of 2 to 30 minutes, for example 10 minutes, in order to avoid, or at least reduce, the non-specific binding of the ligand compound of E-cadherin.

The term "ligand" compound of E-cadherin as used according to the invention is understood to mean a compound that has the capacity to bind specifically to the E-cadherin expressed on the cell membranes. In general, said "ligand" compound binds to the extracellular domain of E-cadherin.

In E-cadherin with the sequence SEQ ID No1, the extracellular peptide portion starts with the amino acid at position 155 and ends with the amino acid at position 697 of the sequence SEQ ID No 1.

In general, a ligand compound that binds to E-cadherin is selected from among nucleic acids or polypeptides that recognise E-cadherin.

By way of illustration, a nucleic acid E-cadherin ligand can easily be selected by those skilled in the art using the SELEX technique. The SELEX method is a method that makes it possible, from a set of nucleic acids with distinct starting sequences, to select one or several nucleic acids that bind specifically to a target molecule of interest, for example a polypeptide target of interest. To implement the SELEX method in order to select a nucleic acid ligand of E-cadherin, those skilled in the art will advantageously refer to the content of the American U.S. Pat. No. 5,475,096 and U.S. Pat. No. 5,270,163.

By way of illustration, a polypeptide ligand of E-cadherin can easily be selected by those skilled in the art, for example using well known double-hybrid techniques, notably described in American U.S. Pat. No. 5,667,973.

Also, a polypeptide ligand of E-cadherin can easily be selected with the help of techniques that use an optical biosensor, such as those described by Edwards and Leatherbarrow (1997, Analytical Biochemistry, 246: 1-6) and also by Szabo et al. (1995, Curr. Opinion Struct. Biol., 5(5): 699-705). This technique makes it possible to detect interactions between two molecules in real time, without needing prior labelling. This technique is based on the phenomenon of surface plasmon resonance (or SPR). By way of a brief explanation, a first partner molecule, for example E-cadherin, is immobilised on a surface such as a carboxymethyl dextran matrix. Then, a second partner molecule, for example a test polypeptide, is incubated with the first partner molecule, then SPR is used to detect the binding or absence of binding, and where appropriate the degree of binding, between the two molecules, for example between E-cadherin and the test polypeptide.

One example of a polypeptide that is a ligand of E-cadherin is beta-catenin, for example the beta-catenin with amino acid sequence SEQ ID No2.

Another example of a polypeptide ligand of E-cadherin is an antibody specifically directed against E-cadherin, and more specifically an antibody directed against the extra-cellular domain of E-cadherin.

The antibodies according to the invention are polyclonal or monoclonal antibodies.

Preferably, polyclonal antibodies are selected from among:

(i) a whole antibody fraction purified from the serum of a mammal immunised against E-cadherin;

(ii) a purified fraction of monospecific polyclonal antibodies directed against E-cadherin;

(iii) Fab or F(ab)'2 fragments prepared from polyclonal antibodies (i) and (ii) above.

Obtaining a whole antibody fraction (i) purified from the serum of a mammal immunised against E-cadherin preferably comprises the following steps:

a) injecting a mammal with a compound comprising E-cadherin or a polypeptide containing the extra-cellular domain of E-cadherin, combined with at least one adjuvant of immunity;

b) recovering the immune serum from the said mammal, which contains the antibodies directed against E-cadherin, c) purifying an antibody fraction from the immune serum.

Each of these steps is described in more detail below. The recovery of the immune serum is carried out in a manner known to those skilled in the art, for example by separating the serum by centrifuging a whole blood sample. The purification of an antibody fraction is carried out starting from the immune serum of an immunised patient, for example by affinity chromatography, precipitation with ammonium sulphate, ion exchange chromatography, gel filtration, Protein A/G chromatography on a column, affinity chromatography, or immunoaffinity chromatography.

A purified fraction of monospecific polyclonal antibodies (ii) directed against E-cadherin can be obtained by carrying out affinity chromatography on a whole antibody fraction (i) purified from the immune serum of a mammal immunised against human E-cadherin, by binding the E-cadherin or an antigen motif of E-cadherin to the column.

The purification of F(ab')$_2$ fragments from polyclonal antibodies described above or from immune serum or blood plasma can be carried out according to the method described in the patent application US2002/0164327, comprising a step of pepsin digestion of blood plasma or serum and steps of separation and purification until F(ab')$_2$ fragments are obtained, free from albumin, entire antibodies, and substantially free from pyrogenic substances.

The isolation of F(ab) and F(ab')$_2$ fractions makes it possible to obtain specific advantages, such as the action of binding to E-cadherin without interacting with other effector molecules of the immune system.

The F(ab) fragments can be obtained by a similar method, consisting of papain digestion of the immune serum, plasma or purified fractions of polyclonal antibodies (i), (ii) and (iii) from a mammal immunised against E-cadherin.

Alternatively, the antibodies are monoclonal and are selected from:
  (i) antibodies produced by cells originating from the cell fusion of (a) B cells of a mammal immunised against human E-cadherin and (b) cells from an antibody-producing cell line, such as myeloma cells;
  (ii) antibodies produced by cells transfected or transformed by DNA encoding an immunoglobulin, said DNA having been previously isolated from the DNA of a B cell of a mammal immunised against human E-cadherin;
  (iii) Fab or F(ab)'$_2$ fragments prepared from polyclonal antibodies (i) and (ii) above;
  (iv) ScFv fragments.

According to the invention, it is possible to use any one of the many commercially available monoclonal or polyclonal antibodies that recognise human E-cadherin. Notably, it is possible to use the anti-E-cadherin antibodies marketed by Zymed, notably the antibodies contained in the ELISA kit referenced no 99-1700. It is also possible to use the anti-E-cadherin monoclonal antibodies marketed by Axxora under the references no ECCD-2, HECD-1 or no SHE78-7, or those marketed by Biocare Medical under the references no CM170A, CM170B, CM170C and PM170AA, or those marketed by Serotec under reference no MCA1482, or those marketed by Acris Antibodies GmbH under reference no SM1531P, or those marketed by under reference no MAB3199, or those marketed by DbioSys under reference no Mob 193. It is also possible to use anti-E-cadherin polyclonal antibodies marketed by Novus Biologicals under the reference no ab15148, or those marketed by AbCam under the reference no ab14015.

Preferably polyclonal or monoclonal antibodies that bind selectively to the extracellular portion of E-cadherin are used.

Advantageously, the anti-E-cadherin monoclonal antibody marketed by Zymed under the reference no 13-1700 is used. This monoclonal antibody recognises the EC1 domain of the extracellular portion of E-cadherin, which is located from the amino acid in position 157 to the amino acid in position 262 of the amino acid sequence SEQ ID No1.

In certain embodiments of step c) of the method, a secondary ligand compound is used that has the capacity to bind to the E-cadherin ligand compound, said secondary ligand compound being labelled with a detectable molecule.

In certain embodiments of step c) of the method, the detection of E-cadherin is achieved by bringing the cell culture into contact with a secondary ligand compound labelled with a detectable molecule, said labelled secondary compound having the capacity to bind to the E-cadherin ligand compound. According to this embodiment, the detection of the complexes formed between the E-cadherin present on the surface of the cell membrane and the E-cadherin ligand compound is carried out by detection of the signal emitted by the labelled secondary compound that binds to the ligand compound involved in the (E-cadherin/E-cadherin ligand compound) complexes. By way of illustration of such an embodiment, the labelled secondary compound may consist of a labelled antibody directed specifically against the E-cadherin ligand compound.

In a particular embodiment of the method, the E-cadherin ligand compound is labelled with a detectable molecule.

Depending on the type of detectable molecule, the presence of E-cadherin on the cell membranes can be monitored by known techniques, notably techniques using measurement of fluorescence with a flow cytometer, a microplate reader, a fluorimeter, or a fluorescence microscope, or by colorimetric, enzymatic, radioactive measurement or immunological techniques. By way of illustration, the detectable molecule can be chosen from among an antigen, a fluorescent protein, a radioactive protein, a receptor protein such as biotin, or a protein having enzymatic activity.

When the detectable protein is an antigen, it can be any type of antigen, so long as the specific antibodies for this antigen are readily available or, alternatively, can be prepared according to any method for preparing antibodies, including polyclonal or monoclonal antibodies, well known to those skilled in the art. Preferably, in this case, the detectable molecule consists of a small sized antigen. So, preferably, a peptide chain of 7 to 100 amino acids in length, more preferably 7 to 50 amino acids in length, or better still, 7 to 30 amino acids in length, for example 10 amino acids in length, is used as the antigen. By way of illustration, the HA antigen with sequence [NH$_2$-YPYDVPDYA-COOH] SEQ ID No 3, or a FLAG antigen with sequence [NH$_2$-DYKDDDDK-COOH] SEQ ID No 4 (FLAG monomer) or with sequence [NH$_2$-MDYKDHDGDYKDHDIDYKDDDDK-COOH] SEQ ID No 5 (FLAG trimer) or an MYC antigen with sequence [NH$_2$-MEQKLISEEDL-COOH] SEQ ID No6 can be used. In this case, to quantify the detectable molecule at step (c) of the method, an antibody specific to the antigen contained in the ligand compound is used, this antibody being directly or indirectly labelled. Then the quantification is done by measuring the detectable signal produced by the complexes formed in the cell preparations, between the labelled antibody and the E-cadherin ligand compound comprising the antigen marker.

When the detectable protein is an intrinsically fluorescent protein, it is notably selected from the GFP protein or one of its derivatives, the YFP protein or one of its derivatives, and the dsRED protein. For instance, among the proteins derived from the GFP protein, one of the proteins known by the names GFPMut3, Venus, Sapphire etc. can be used. For instance, one of the intrinsically fluorescent proteins described in the American U.S. Pat. No. 5,625,048, U.S. Pat. No. 5,777,079, U.S. Pat. No. 5,804,387, U.S. Pat. No. 5,968,738, U.S. Pat. No. 5,994,077, U.S. Pat. No. 6,054,321, U.S. Pat. No. 6,066,476, U.S. Pat. No. 6,077,707, U.S. Pat. No. 6,090,919, U.S. Pat. No. 6,124,128, U.S. Pat. No. 6,172,188, or the European patents no EP 851 874 et EP 804 457 can be used.

When the detectable protein is an intrinsically fluorescent protein, the detectable protein is quantified at step (b) of the method by measuring the fluorescent signal emitted by the fluorescent protein using any appropriate device. So, at step (b), when the first detectable protein is a fluorescent protein, said detectable protein is quantified by measuring the fluorescent signal emitted by said protein.

When the detectable protein is a protein with enzymatic activity, said detectable protein is chosen, for instance, from luciferase and β-lactamase. In this case, the detectable molecule is quantified at step (c) of the method by measuring the amount of compound or compounds produced by enzymatic conversion of the substrate. When the product of enzymatic activity is coloured, the measurement can be done by colorimetry. When the product of enzymatic activity is fluorescent, the intensity of the fluorescent signal emitted by said product is measured using any suitable device for measuring fluorescence. Thus, in step (b), when the first detectable molecule is a protein having enzymatic activity, said detectable protein is quantified by measuring the quantity of substrate modified by said protein, generally by measuring the optical density at the wavelength of the substrate emission.

In certain embodiments of the method of the invention, the ligand compound consists of a biotin coupled anti-E-cadherin antibody or a secondary antibody directed against the mammal in which the biotin coupled anti-E-cadherin antibody was produced. In these particular embodiments, a labelled secondary compound containing streptavidin can be used. An example illustrating such a labelled secondary compound is a fusion protein between streptavidin and a detectable molecule selected from the detectable molecules defined above, including a detectable molecule consisting of an enzyme. For example, a labelled secondary compound consisting of a streptavidin molecule coupled or fused with horseradish peroxidase or the peroxidase anti-peroxidase (PAP) soluble complex system (marketed by SIGMA, P3039) can be used. According to this last system, the secondary compound is complex. This complex secondary compound comprises (i) an antibody directed against an anti-E-cadherin antibody, and more specifically against the Fc portion of the said anti-E-cadherin antibody and (ii) an antibody directed against a peroxidase, such as horseradish peroxidase or soy peroxidase, the said antibody being complexed with the said peroxidase, at the antigen recognition domain (CDR). In this system, the antibody directed against the anti-E-cadherin antibody can be for example a mouse anti-antibody, when the anti-E-cadherin antibody consists of a mouse antibody. According to this system, two peroxidase molecules are bound to the anti-peroxidase antibody, which is a technical advantage and gives the method an increased sensitivity threshold, compared with many other systems of labelling and detection.

Thus, according to this system, the detection of the E-cadherin exposed on the membrane surface of the cells can be carried out using (i) an anti-E-cadherin antibody, to which is bound (ii) an antibody directed against the anti-E-cadherin antibody, to which is bound (iii) an anti-peroxidase antibody complexed with peroxidase at its antigen recognition site (CDR).

The presence of complexes between E-cadherin and a peroxidase labelled E-cadherin ligand, fixed to the cell membrane surface can be revealed by optical detection of the product resulting from the conversion of a horseradish peroxidase substrate, such as ortho-phenylene diamine (OPD), after the labelled secondary compound has been brought into contact with the E-cadherin/ligand complexes.

A further object of this invention is also a set or kit for screening anticancer substances comprising:
a) tumour cells which do not express E-cadherin on their cell membrane;
b) a ligand compound of E-cadherin.

The tumour cells included in the kit of the invention can be selected from among the tumour cells described in the present specification.

Advantageously, the kit comprises tumour cells that have the capacity to form metastases that are selected from among the following cell lines: SW620 (ATCC no CCL-227), SKCo-1 (ATCC no HTB-39), CoLo205 (ATCCno CCL-222), and HCT116 (ATCC no CCL-247) rendered p21-deficient.

In a kit according to the invention, the E-cadherin ligand compound may be one of the E-cadherin ligand compounds described in the present specification.

Advantageously, an E-cadherin ligand compound is used that binds to the extracellular portion of E-cadherin.

According to a particular embodiment of the above kit, the E-cadherin ligand compound consists of an anti-E-cadherin polyclonal or monoclonal antibody.

Biotin-coupled antibodies are encompassed in the set of anti-E-cadherin antibodies likely to be included in a kit according to the invention.

In certain embodiments of a screening kit of the invention, said kit also comprises a secondary ligand compound of the type previously described in the present specification. The said secondary ligand compound can consist of a secondary ligand compound that binds to the E-cadherin ligand compound, said secondary ligand compound being labelled with a detectable molecule.

Advantageously, when the E-cadherin ligand compound consists of a biotin-coupled anti-E-cadherin antibody, the secondary ligand compound is selected from among the compounds resulting from the coupling between streptavidin and a detectable molecule, for example between streptavidin and an enzyme. By way of illustration, a compound resulting from the coupling between streptavidin and horseradish peroxidase can be used as a secondary ligand compound.

According to another embodiment of the kit according to the invention, the secondary ligand compound consists of an antibody directed against the anti-E-cadherin antibody, for example an antibody directed against the anti-E-cadherin antibody that is labelled with a detectable molecule.

According to a specific embodiment of an anti-E-cadherin antibody labelled with a detectable molecule, an anti-E-cadherin antibody is used, to which is bound (ii) an anti peroxidase antibody that is recognised by the antibody directed against anti-E-cadherin antibodies, the said anti-peroxidase antibodies being bound to two peroxidase molecules at their antigen binding site (CDR).

This invention also relates to the use of a ligand compound of the extracellular portion of E-cadherin for in vitro screening of anticancer substances. Preferably, the ligand compound is used in conjunction with a culture of tumour cells which do not express E-cadherin on their cell membrane.

This invention also relates to the use of a ROCK ("Rho-associated coiled-coil forming protein serine/threonine kinase") kinase inhibitor for the production of a pharmaceutical composition directed to the prevention or treatment of a cancer, notably a cancer selected from among those defined in the present description. More particularly, a ROCK kinase protein inhibitor is used for the production of an anti-metastatic drug.

A ROCK kinase inhibitor may be selected from the group consisting of Y-27632 marketed by VWR INTERNATIONAL (REF: 688 000-5).

The present invention is also illustrated by the following drawings and examples.

DRAWINGS

FIG. 1 illustrates the effect of the inhibitor Y-27632, which is a ROCK kinase inhibitor, on the correct localisation of E-cadherin on the intercellular junctions in several cancerous cell lines. FIGS. A1 to A5: control cells without inhibitor. FIGS. B1 to B5: cells incubated with the inhibitor Y-27632. Columns 1 and 2: non-metastatic cancer cells hct116 (1) and SW480 (2). Columns 3 to 5: metastatic cancerous cells SW620 (3), SKCo-1 (4) and CoLo205 (5).

Figure 2:
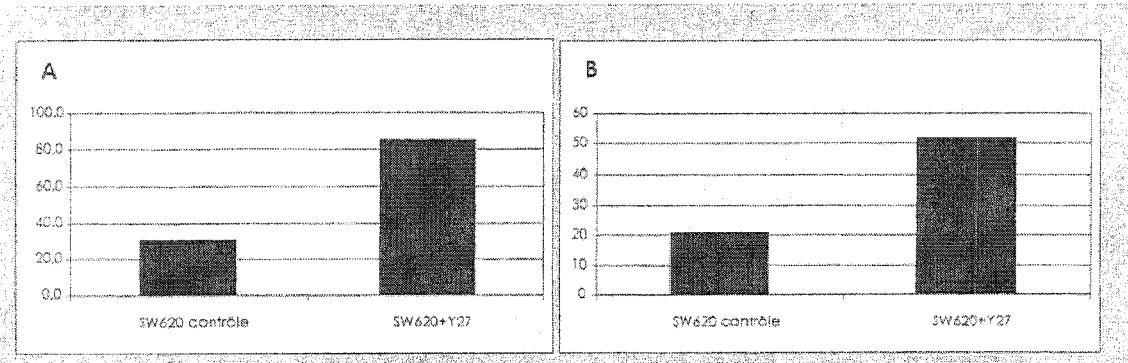

FIG. 2 illustrates the effect of the treatment of metastatic cells of the SW620 cell line by the inhibitor Y-27632 on the spreading ability of the cells (FIG. 2A) and on the formation of E-cadherin type adhesion junctions (FIG. 2B). In FIGS. 2 A and 2 B: on the left: control cells without inhibitor; on the right: cells incubated with Y-27632. On the x-axis: the percentage of flat cells (FIG. 2A) or the percentage of cells forming E-cadherin type intercellular junctions (FIG. 2B).

Figure 3:
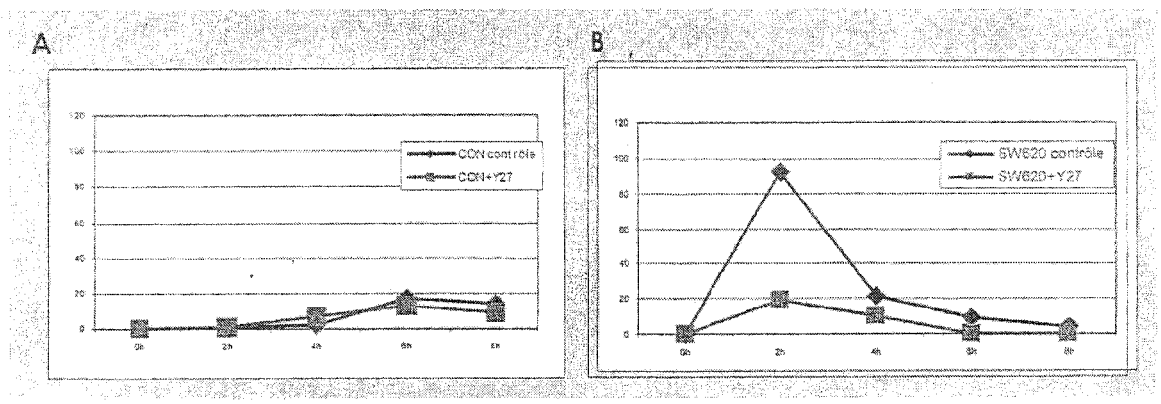

FIG. 3 illustrates a comparison of the effect of the treatment with the inhibitor Y-27632 on the invasive potency of normal colon cells from the cell line CoN (FIG. 3A) and metastatic cells from the SW620 cell line (FIG. 3B). On the x-axis: migration time in the presence or absence of Y-27632. On the y-axis: mean number of cells per field having crossed through the reconstituted cell matrix (microscope, OBJ×20).

EXAMPLES

Example 1

Identification of a strict correlation between the formation of E-cadherin type intercellular junctions and the reversion of cancer cells to the non-metastatic phenotype.

A. Materials and Methods
1. Protocol for Immunofluorescent Labelling of e-Cadherin
1—The cells are plated in 6-well plates, each well containing 3 glass coverslips 10 mm in diameter.
2—Place the cells in 0% Serum for 18 to 24 hours then treat them or not with Y27 10 μM+PDGF 5 ng/ml for 36 to 48 h.
3—Fix the cells for 10 minutes with formalin (3.7% formaldehyde in PBS).
4—Saturation, 10 minutes PBS-BSA
5—Incubation of the primary antibody, diluted to 1:500 in PBS-BSA, 2 hours at 37° C. (Mouse anti E-cadherin, ZYMED, ref: 13-1700)
6—2 rapid washes in PBS-0.1% Tween
7—Incubation of the secondary antibody (Alexa Fluor® 488 F(ab')$_2$ fragment of goat anti mouse IgG, Molecular Probes ref: A-11017), diluted to 1:2000 in PBS-BSA, 30 minutes at 37° C.
8—2 rapid washes in PBS-0.1% Tween
9—Mounting in Mowiol medium between the slide and the coverslip.
2. Invasion Test
1—On D-2, thaw the Matrigel at 4° C. all night
2—On D-1 measure the Matrigel into insert chambers:
Put all the necessary material on ice (Matrigel, culture medium, tips, eppendorfs, etc. . . . ).
Put the FluoroBlock inserts (FALCON, ref: 351152) in the 24-well plates (FALCON, ref: 353504).
Dilute the Matrigel to 2 mg/ml in cold serumless medium (if the cells are to be subjected to a treatment X, include the product in the Matrigel, e.g.: Y 27632)
Aliquot 100 μl of 2 mg/ml Matrigel per insert avoiding creating bubbles.
Leave O/N at 37° C. in a humid atmosphere (in an incubator)
3—On D day, plate the cells on the Matrigel:
First put 700 μl of 10% serum medium in a 24-well plate and transfer the inserts to this plate.
Trypsinate the cells (previously treated or not . . . ) and take them up in 2% serum medium.
Plate 50 000 cells per insert in 200 μl of 2% serum medium on the Matrigel (optionally put Y27632 into the plated cells).
4—The migration time varies depending on the cell type but generally allowing them to migrate for 8 hours fixing a point every 2 hours seems suitable.
To fix them, transfer the inserts to a 24-well plate containing 1 ml of formalin (3.7% formaldehyde in PBS), suck up the culture medium inside the chambers and also add formalin (very important, prevents the cells from continuing to migrate in the Matrigel). Incubate for 10 minutes.
Wash 3 times rapidly in PBS
Then, label with propidium iodide by incubating the inserts in 1 ml of propidium iodide (SIGMA, ref: P-4864) 1:500 in PBS, O/N at 4° C., in the dark.
3. Protocol for Labelling e-Cadherin in 96-Well Plates
1—For the colorectal cell lines, plate about 10 000 cells per well (in 96-well plates Falcon, ref: 353072).
2—Carry out the necessary treatments (control, Y27, PDGF . . . for 48 hours) and fix for 10 minutes in formalin (3.7% formaldehyde in PBS)
3—Saturation, 10 minutes PBS-BSA
4—Incubation of the primary antibody, diluted to 1:500 in PBS-BSA, 2 hours at 37° C. (Mouse anti-E-cadherin, ZYMED, ref: 13-1700)
5—2 rapid washes in PBS-0.1% Tween
6—Incubation with biotinylated anti-mouse Ab, dilution 1:1000 in PBS-BSA, 30 minutes at 37° C., (Anti-Mouse IgG, Heavy and light chain specific biotin conjugate, CALBIOCHEM, ref: 401213)
7—2 rapid washes in PBS-0.1% Tween
8—Incubation with Streptavidin-HRP, dilution 1:1000 in PBS-BSA, 30 minutes at 37° C., (ECL Streptavidin-Horseradish Peroxidase conjugate, AMERSHAM BIOSCIENCES, ref: RPN1231)
9—2 rapid washes in PBS-0.1% Tween
10—Revealing:
Dissolve one capsule of Phosphate-citrate buffer containing sodium perborate" (SIGMA, ref: P4922) in 100 ml of deionised water. This buffer must be used within 30 minutes of being reconstituted.
Dissolve tablets of o-Phenylenediamine (OPD) dihydrochloride (SIGMA, ref: P6787) in this buffer to obtain a final concentration of 0.4 mg/ml (1 tablet of 10 mg OPD in 40 ml of perborate buffer).
Put 100 μl of OPD/Perborate per well and incubate at ambient temperature for 5 minutes.
Stop the reaction with 50 μl of 3N HCl.
Read the OD at 490 nm.

B. Results

It has been shown that the phenotype of SW620 metastatic cells, that is a round phenotype associated with a lack of E-cadherin type junctions and a high invasive power, can be made to revert by a ROCK kinase inhibitor, Y-27632. This kinase is a powerful migration activator and has already been involved in invasive phenomena. It has been shown that treating cells from the SW620 metastatic cell line with Y-27632 enhances the spreading ability of these cells (FIG. 2A) and the formation of E-cadherin dependent junctions (FIG. 1B and FIG. 2B). It has been shown that treating these cells with Y-27632 also makes it possible to drastically reduce their invasive capacity. After treatment with Y-27632, the SW620 metastatic cells have a very low level of invasion, comparable to that of CoN normal colon cells (FIG. 3B).

As illustrated in FIG. 1, the treatment of the colorectal cells with ROCK kinase inhibitor (Y-27632) causes correct relocation of E-cadherin at the junctions of the metastatic cell lines (SW620, SKCo-1 and CoLo205 cell lines). FIG. 1A illustrates the location of E-cadherin in different colorectal control cell lines. FIG. 1B illustrates the location of E-cadherin in different colorectal cell lines treated with ROCK kinase inhibitor (Y-27632, 10 µM for 48 hours).

As illustrated in FIG. 2, treating cells from the SW620 metastatic cell line with ROCK kinase inhibitor (Y-27632) leads to the flattening of these cells and the formation of E-cadherin type junctions. In FIG. 2A, 30% of the SW620 control cells exhibit a flat phenotype and 70% a round phenotype. After treatment with Y-27632, 90% of the cells are flat and only 10% retain a round phenotype. In FIG. 2B, 22% of SW620 control cells are capable of forming junctions. After treatment with Y-27632, 52% of the cells are capable of forming E-cadherin type junctions.

In conclusion, the E-cadherin dependent junction forming tests (FIG. 2) carried out in parallel with the invasion tests (FIG. 3) have made it possible to show, in the model of SW620 metastatic colon cells, that a strict correlation exists between the ability to re-form E-cadherin type junctions and a decrease in the invasive capacity.

Example 2

Illustration of an Embodiment of the Screening Method According to the Invention 1—Plate about 10 000 cells per well for the colorectal cell lines in Falcon 96-well plates, (ref: 3530072).
2—Carry out the necessary treatments (control, Y27, PDGF . . . for 48 hours) and fix for 10 minutes in formalin (3.7% formaldehyde in PBS)
3—Saturation, 10 minutes PBS-BSA
4—Incubation of the primary antibody, diluted to 1:500 in PBS-BSA, 2 hours at 37° C. (Mouse anti-E-cadherin, ZYMED, ref: 13-1700)
5—2 rapid washes with PBS-0.1% Tween.
6—Incubation of the biotinylated anti-mouse antibodies, dilution 1:1000 in PBS-BSA, 30 minutes at 37° C. (Anti-Mouse IgG, Heavy and light chain specific biotin conjugate, CALBIOCHEM, ref: 401213).
7—2 rapid washes with PBS-0.1% Tween.
8—Incubation Streptavidin-HRP, dilution 1:1000 in PBS-BSA, 30 minutes at 37° C., (ECL Streptavidin-Horseradish Peroxidase conjugate, AMERSHAM BIOSCIENCES, ref: RPN1231)
9—2 rapid washes with PBS-0.1% Tween.
10—Revealing:
a) Dissolve one capsule of "Phosphate-citrate buffer containing sodium perborate" (SIGMA, ref: P4922) in 100 ml of deionised water. This buffer must be used within 30 minutes of being reconstituted.
b) Dissolve tablets of o-Phenylenediamine (OPD) dihydrochloride (SIGMA, ref: P6787) in this buffer to obtain a final concentration of 0.5 mg/ml (1 tablet of 10 mg OPD in 40 ml of perborate buffer).
c) Put 100 µl of OPD/perborate per well and incubate at ambient temperature for 5 minutes.
d) Stop the reaction with 50 µl of 3N HCl.
e) Read the OD at 490 nm.

The invention claimed is:

1. A method for screening anti-metastatic anticancer substances which do not act directly on the expression of E-cadherin, said method comprising the following steps:
   a) growing tumour cells with the capacity for forming metastases and which do not express E-cadherin on their cell membrane;
   b) brining the cultivated cells obtained at the end of step a) into contact with a candidate substance or a combination of candidate substances;
   c) detecting, in the culture of cells obtained at the end of step b), the presence of E-cadherin at the cell surface; and
   d) positively selecting the candidate substance, or the combination of candidate substances, when the E-cadherin has been detected at step c),
   wherein the tumour cells that have the capacity to from metastases are from cell lines selected from the group consisting of: SW620 (ATTC No. CCL-227), SKCo-1 (ATTC No. HTB-39) and CoLo205 (ATTC No. CCLL-222).

2. The method according to claim 1, wherein at step c), the detection is carried out by bringing the cells obtained at the end of step b) into contact with a ligand compound of E-cadherin.

3. The method according to claim 2, wherein the E-cadherin ligand compound binds to the extracellular portion of E-cadherin.

4. The method according to claim 2, wherein the ligand compound is labelled with a detectable molecule.

5. The method according to claim 2, wherein at step c), a secondary ligand compound that binds to the E-cadherin ligand compound is used, the said second ligand compound being labelled with a detectable molecule.

6. The method according to claim 2, wherein the ligand compound consists of an anti-E-cadherin antibody.

7. The method according to claim 6, wherein at step c), a secondary ligand compound that binds to the anti-E-cadherin antibody is used, the said second ligand compound being labelled with a detectable molecule.

8. The method according to claim 7, wherein the secondary ligand compound comprises a streptavidin molecule coupled to, or fused with, an enzyme.

9. The method according to claim 7, wherein the second ligand compound is an antibody directed against the anti-E-cadherin antibody.

* * * * *

SEQUENCE LISTING

```
<160> NUMBER OF SEQ ID NOS: 6

<210> SEQ ID NO 1
<211> LENGTH: 882
<212> TYPE: PRT
<213> ORGANISM: Homo sapiens

<400> SEQUENCE: 1

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125         Pro His

Gln Ala Ser Val Ser Gly Ile Gln Ala Glu Leu Leu Thr Phe Pro Asn
    130                 135                 140
```

```
Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
            165                 170                 175

Gln Ile Lys Ser Asn Lys Asp Lys Glu Gly Lys Val Phe Tyr Ser Ile
        180                 185                 190

Thr Gly Gln Gly Ala Asp Thr Pro Pro Val Gly Val Phe Ile Ile Glu
    195                 200                 205

Arg Glu Thr Gly Trp Leu Lys Val Thr Glu Pro Leu Asp Arg Glu Arg
210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
    530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
```

```
                565                 570                 575
Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Ile Asp Ala Asp Leu Pro Pro Asn Thr Ser
    610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
            645                 650                 655

Ala Leu Glu Val Gly Asp Tyr Lys Ile Asn Leu Lys Leu Met Asp Asn
        660                 665                 670

Gln Asn Lys Asp Gln Val Thr Thr Leu Glu Val Ser Val Cys Asp Cys
    675                 680                 685

Glu Gly Ala Ala Gly Val Cys Arg Lys Ala Gln Pro Val Glu Ala Gly
690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
        755                 760                 765

Leu Ser Gln Leu His Arg Gly Leu Asp Ala Arg Pro Glu Val Thr Arg
    770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
    850                 855                 860

Trp Gly Asn Arg Phe Lys Lys Leu Ala Asp Met Tyr Gly Gly Gly Glu
865                 870                 875                 880

Asp Asp

<210> SEQ ID NO 2
<211> LENGTH: 781
<212> TYPE: PRT
<213> ORGANISM: Homo sapiens

<400> SEQUENCE: 2

Met Ala Thr Gln Ala Asp Leu Met Glu Leu Asp Met Ala Met Glu Pro
1               5                   10                  15

Asp Arg Lys Ala Ala Val Ser His Trp Gln Gln Gln Ser Tyr Leu Asp
            20                  25                  30

Ser Gly Ile His Ser Gly Ala Thr Thr Thr Ala Pro Ser Leu Ser Gly
        35                  40                  45

Lys Gly Asn Pro Glu Glu Glu Asp Val Asp Thr Ser Gln Val Leu Tyr
    50                  55                  60
```

-continued

```
Glu Trp Glu Gln Gly Phe Ser Gln Ser Phe Thr Gln Glu Gln Val Ala
 65                  70                  75                  80

Asp Ile Asp Gly Gln Tyr Ala Met Thr Arg Ala Gln Arg Val Arg Ala
                 85                  90                  95

Ala Met Phe Pro Glu Thr Leu Asp Glu Gly Met Gln Ile Pro Ser Thr
            100                 105                 110

Gln Phe Asp Ala Ala His Pro Thr Asn Val Gln Arg Leu Ala Glu Pro
        115                 120                 125

Ser Gln Met Leu Lys His Ala Val Val Asn Leu Ile Asn Tyr Gln Asp
    130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                165                 170                 175

Gln Leu Ser Lys Lys Glu Ala Ser Arg His Ala Ile Met Arg Ser Pro
            180                 185                 190

Gln Met Val Ser Ala Ile Val Arg Thr Met Gln Asn Thr Asn Asp Val
        195                 200                 205

Glu Thr Ala Arg Cys Thr Ala Gly Thr Leu His Asn Leu Ser His His
    210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
        275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
        355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400

Leu Leu Gly Thr Leu Val Gln Leu Leu Gly Ser Asp Asp Ile Asn Val
                405                 410                 415

Val Thr Cys Ala Ala Gly Ile Leu Ser Asn Leu Thr Cys Asn Asn Tyr
            420                 425                 430

Lys Asn Lys Met Met Val Cys Gln Val Gly Gly Ile Glu Ala Leu Val
        435                 440                 445

Arg Thr Val Leu Arg Ala Gly Asp Arg Glu Asp Ile Thr Glu Pro Ala
    450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
```

```
            485                 490                 495
Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
            515                 520                 525

Glu Gln Gly Ala Ile Pro Arg Leu Val Gln Leu Leu Val Arg Ala His
            530                 535                 540

Gln Asp Thr Gln Arg Arg Thr Ser Met Gly Thr Gln Gln Gln Phe
545                 550                 555                 560

Val Glu Gly Val Arg Met Glu Glu Ile Val Glu Gly Cys Thr Gly Ala
                    565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
            595                 600                 605

Asn Ile Gln Arg Val Ala Ala Gly Val Leu Cys Glu Leu Ala Gln Asp
            610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                    645                 650                 655

Ala Val Leu Phe Arg Met Ser Glu Asp Lys Pro Gln Asp Tyr Lys Lys
                    660                 665                 670

Arg Leu Ser Val Glu Leu Thr Ser Ser Leu Phe Arg Thr Glu Pro Met
                    675                 680                 685

Ala Trp Asn Glu Thr Ala Asp Leu Gly Leu Asp Ile Gly Ala Gln Gly
                    690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                    725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
            755                 760                 765

Gly Asp Ser Asn Gln Leu Ala Trp Phe Asp Thr Asp Leu
            770                 775                 780

<210> SEQ ID NO 3
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 3

Tyr Pro Tyr Asp Val Pro Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 4

Asp Tyr Lys Asp Asp Asp Asp Lys
```

```
<210> SEQ ID NO 5
<211> LENGTH: 23
<212> TYPE: PRT
<213> ORGANISM: Artificial Sequence
<220> FEATURE:
<223> OTHER INFORMATION: synthetic polypeptide

<400> SEQUENCE: 5

Met Asp Tyr Lys Asp His Asp Gly Asp Tyr Lys Asp His Asp Ile Asp
1               5                   10                  15

Tyr Lys Asp Asp Asp Asp Lys
            20

<210> SEQ ID NO 6
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 6

Met Glu Gln Lys Leu Ile Ser Glu Glu Asp Leu
1               5                   10
```